United States Patent [19]

Johnson

[11] 4,219,025
[45] Aug. 26, 1980

[54] ELECTRICALLY HEATED SURGICAL CUTTING INSTRUMENT

[75] Inventor: Donald M. Johnson, Painted Post, N.Y.

[73] Assignee: Corning Glass Works, Corning, N.Y.

[21] Appl. No.: 961,188

[22] Filed: Nov. 16, 1978

[51] Int. Cl.² .................................. A61B 17/38
[52] U.S. Cl. ...................... 128/303.1; 219/233; 219/241
[58] Field of Search ........... 128/303.1, 303.13, 303.14, 128/303.17, 303.18; 30/140; 219/240, 241, 233, 227–229

[56] References Cited

U.S. PATENT DOCUMENTS

| | | | |
|---|---|---|---|
| 3,286,077 | 11/1966 | Radford et al. | 219/241 X |
| 3,634,652 | 1/1972 | Shimizu et al. | 128/303.18 X |
| 3,826,263 | 7/1974 | Cage et al. | 128/303.1 |
| 3,933,157 | 1/1976 | Bjurwill | 128/303.14 |
| 4,074,719 | 2/1978 | Semm | 128/303.1 |
| 4,089,336 | 5/1978 | Cage et al. | 128/303.1 |

FOREIGN PATENT DOCUMENTS 1139926  11/1962  Fed. Rep. of Germany ...... 128/303.17

Primary Examiner—Lee S. Cohen
Attorney, Agent, or Firm—John P. DeLuca; Burton R. Turner

[57] ABSTRACT

A surgical cutting instrument includes an electrically heated cutting edge and a power supply system for maintaining the cutting edge at a constant high temperature for sterilizing the blade, cutting tissue and cauterizing the incised tissue to reduce hemorage from the cut surfaces of the tissues (hemostasis).

10 Claims, 3 Drawing Figures

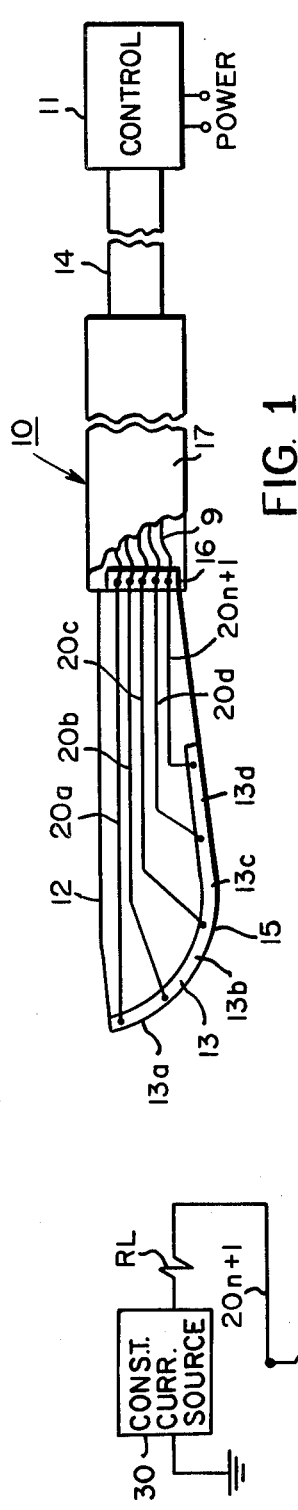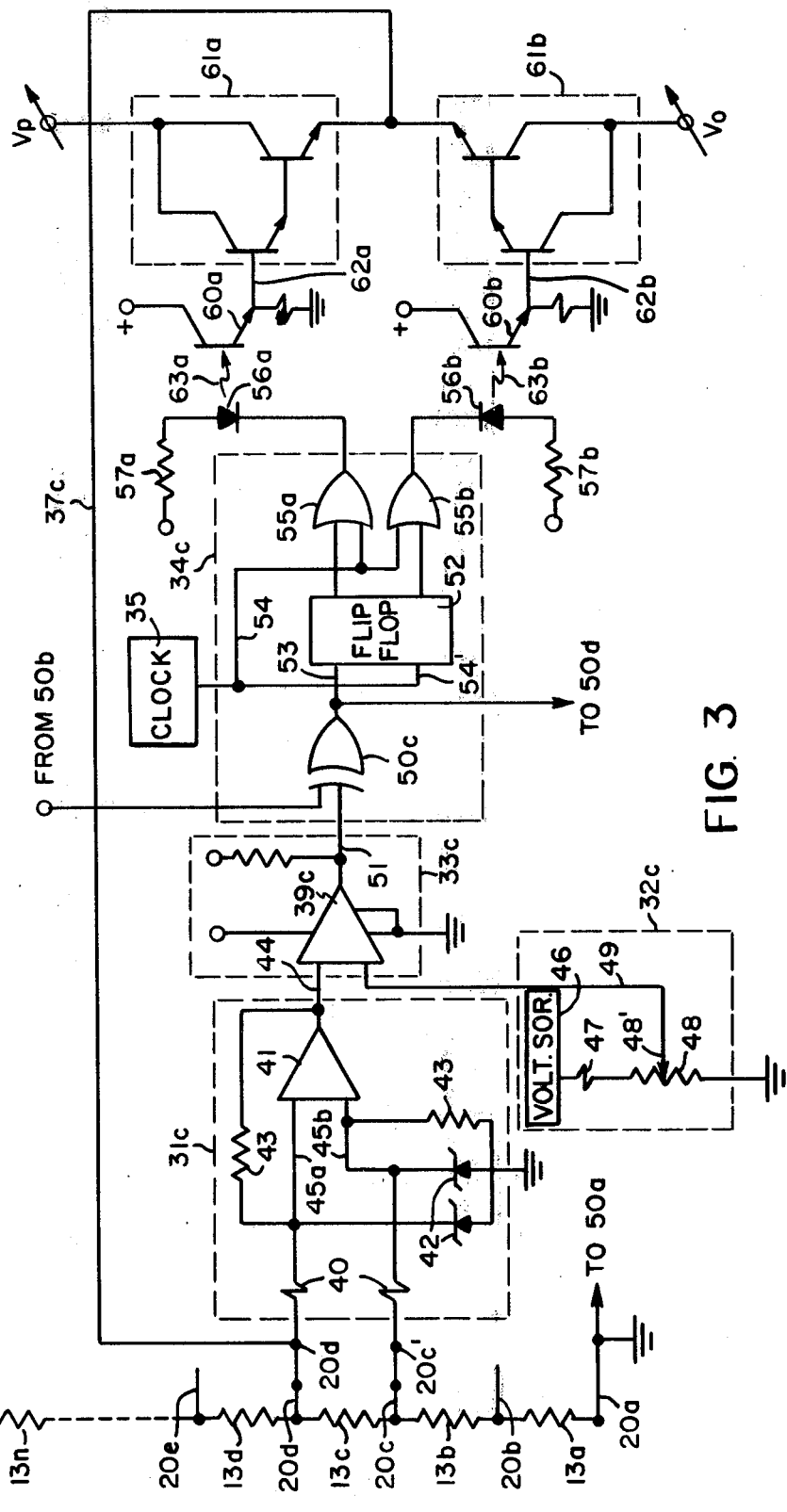

ELECTRICALLY HEATED SURGICAL CUTTING INSTRUMENT

BACKGROUND OF THE INVENTION

The control of bleeding during surgery accounts for a major proportion of the total time involved in an operation. The bleeding that occurs when tissue is incised obscures the surgeon's vision, reduces his precision and often dictates slow and elaborate procedures in a surgical operation. Each bleeding vessel must be grasped in pincer like clamps to stop the flow of blood and the tissue and vessel within each clamp must then be tied with pieces of fine thread. These ligated masses of tissue die and decompose and thus tend to retard healing and promote infection.

The invention described herein is a hemostatic surgical cutting instrument incorporating an electrically heated edge, where it is desirable to minimize a number of external electrical connections to a series of electrical elements.

Accordingly, the present invention provides a surgical cutting instrument having a heated element which is electrically heated to a constant high temperature for sterilizing the blade, and cauterizing the surfaces of the incision, thereby allowing surgery to be more rapidly performed. It is accomplished in accordance with the illustrated embodiment of this invention by providing an electrically heated element adjacent the cutting edge of the blade and by providing a control system which maintains the heated element at a high substantially constant temperature during its use.

The temperature at which the cutting edge of the blade is maintained depends upon such factors as the nature of the tissue to be cut, the speed of the cutting desired, the degree of tissue coagulation desired and the nonadherence of the blade to the incised tissue and generally is maintained between 200°-300° C. for typical incisions. The handle of the cutting instrument is thermally insulated from the blade to permit comfortable use of the instrument and the handle and blade with its electrically heated cutting edge are detachable for easy replacement and interchangeability.

SUMMARY OF THE INVENTION

According to the present invention the instantaneous temperature of the cutting edge is monitored by measuring the resistance of the heating element or elements and the monitoring signal thus derived provides an inferred value for temperature which may be used to control the power applied to portions or segments of the heating element.

DESCRIPTION OF THE DRAWINGS

FIG. 1 is a schematic diagram showing a hemostatic cutting instrument according to a preferred embodiment of the present invention.

FIG. 3 illustrates schematically the control system of FIG. 2 in greater detail with an equivalent circuit for the heating element shown.

DESCRIPTION OF THE PREFERRED EMBODIMENT

Figure 2:
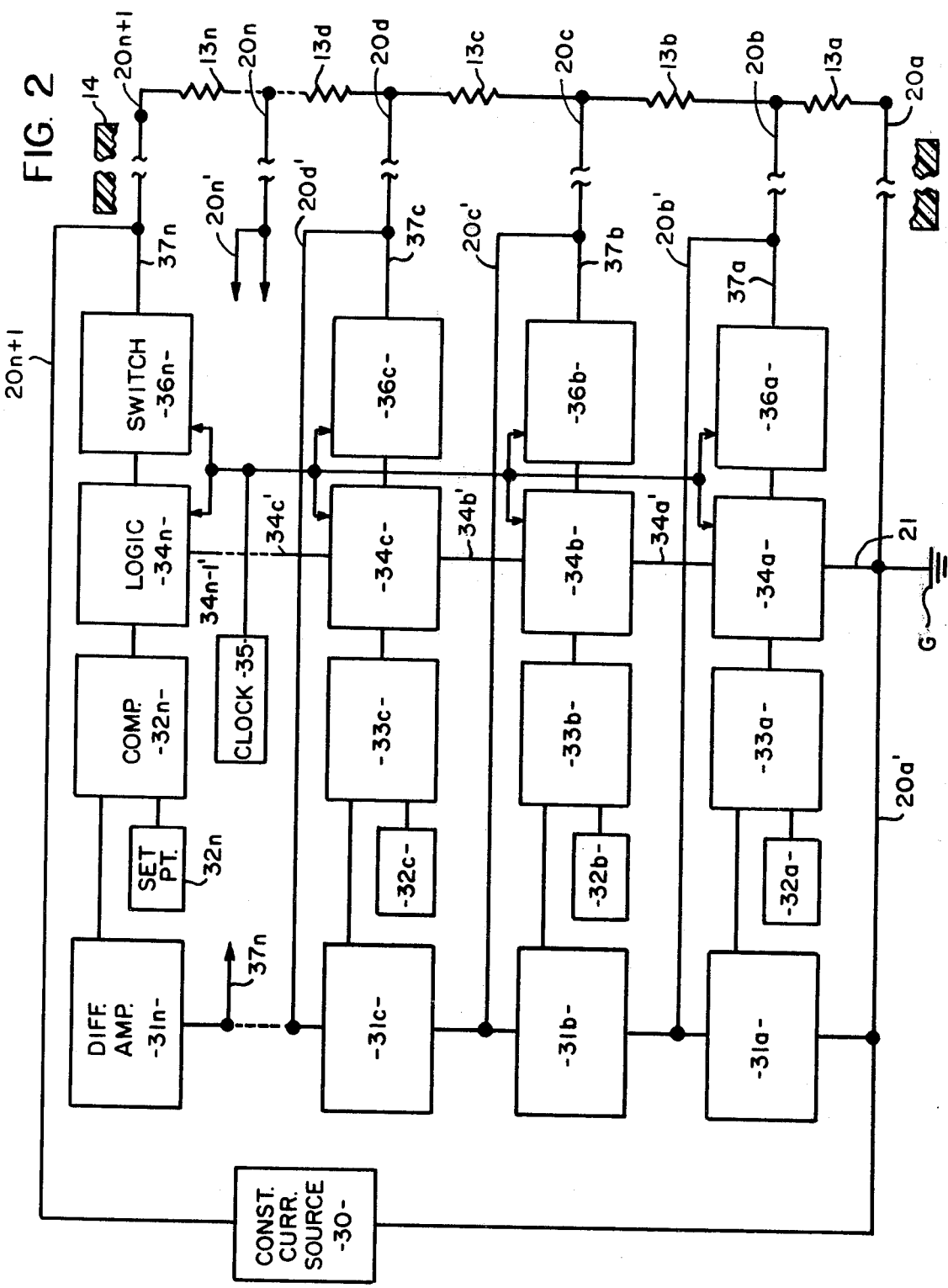
FIG. 2 is a block diagram illustrating schematically the control concept of the present invention with an equivalent circuit for the heating element shown.

Referring now to FIG. 1 of the drawing there is shown one side of surgical cutting instrument 10 connected to a temperature measuring and power controlling system or control 11. The cutting instrument 10 includes a thin glass, glass-ceramic, or ceramic card which may be hereinafter referred to as a substrate or blade 12 in the desired shape of a surgical cutting blade which is detachable from handle or holder 17. An electrically energized heating element 13 is disposed along leading edge 15 of the blade 12 hereinafter referred to as the cutting edge 15. The heating element 13 is connected to the control circuit 11 via a cable 14, having a selected number of conductors 9, and connector 16 in handle 17.

The heating element 13 may be a single filament attached to the edge of the blade 12, for example a layer of electrically conductive material vapor deposited along the cutting edge 15 of blade 12 such as tin oxide. In a preferred embodiment the material used in heating element 13 should have a negative temperature coefficient of resistance, so that, as selected portions of the element cool when in contact with tissue, the resistance of such portions will increase and thereby provide an indication of those portions of the heating element 13 in which additional power should be supplied by the control system 11. The temperature of the heating element 12 may thus be maintained substantially constant along the entire length thereof as portions thereof contact tissue. Suitable materials having a negative temperature coefficient of resistance include silicon carbide, carbon, boron silicate, and such semiconductor materials as silicon and germanium and also antimony doped tin oxides. Of course, materials having a positive coefficient of resistance may also be used as a sensing element of temperature.

For general cutting applications the heating element 13 may consist of a plurality of electrically isolated elements or segments 13a-13d, as shown in FIG. 1, with each of the elements 13a-13d connected to a separate temperature measuring and power controlling portion of the control system 11. For purposes of explanation of FIG. 1 only four segments 13a-13d are illustrated, but more may be provided within the limits of space on substrate 12. In a preferred embodiment the substrate 12 carries eight segments on each side of the blade 12. The back side not shown is a mirror image of the profile illustrated. In FIGS. 2 and 3 the circuits illustrate a system having N segments. Such control system 11 is hereinafter described.

In a preferred embodiment the heating element 13 of hemostatic surgical cutting instrument 10 is formed as a continuous electrically conducting film deposited on each side of the cutting edge 12 with portions of the heating element 13 electrically segmented from other portions as illustrated by reference numerals 13a-13d. For each segment 13a for example a pair of leads 20a and 20b are deposited or printed on the body of the substrate 12 and may be adapted to be coupled with the cable 14 by connectors 16. The leads 20a and 20b form a portion of the power circuit for the segment 13a. Similarly leads 20b and 20c form portions of a circuit for the segment 13b and likewise down through connectors 20d and 20n+1 for segment 13d. Leads 20a and 20n+1 are coupled to the extreme ends of the heating element 13 as illustrated and may act as test leads in addition to their power carrying function. As test leads, the conductors 20a and 20n+1 are provided with an input from the control system 11 for delivering a test current to the heating element 13 which will assist in the measurement of the various resistances (and thus inference of temperature) of the various segments 13a–13d.

It should be understood that the surgical cutting instrument of the present invention is a rather small device and the space requirements on the substrate 12 severely restrict the circuitry which may be printed or deposited thereon. Thus the present invention provides for a means by which the number of leads printed on the substrate 12 may be reduced without a sacrifice of available control for each of the segments 13a through 13d. Furthermore the control system 11 of the present invention is adapted to control each of the segments 13a–13d independently of the other segments by allowing the potential across any one segment 13a through 13d to float between selected values which is sufficient to maintain that segment at the desired temperature. Other sections adjacent thereto may be maintained at the same or different floating potentials independent of the one just described and thus each segment may be independently controlled with a minimum number of electrical connections thereto.

In FIG. 2 the control system 11 of FIG. 1 is detailed. An equivalent circuit of n series resistors represents the heating element 13 and is labeled as each segment 13a–13n. Leads 20a through 20n+1 are coupled as in FIG. 1. Leads 20a and 20n+1 act as test current leads hereinafter described.

A constant current source 30 provides a test current input over the lines 20a' and 20n+1' coupled to respective leads 20a and 20n+1 on blade 12 which are in turn serially connected to the opposite ends of the heating element 13. Each element 13a through 13n represents a series resistance portion of the heating element 13 and each of the leads 20a through 20n+1 is paired with at least one other lead to a corresponding segment 13a–13n.

The constant current source 30 provides a test current input to each segment of the heating element 13 via serial circuit including load resistor RL, lead 20n+1, segments 13a–13n and lead 20a to ground. Depending upon the resistance (inferred temperature) of each segment 13a through 13n, a different voltage drop will be detected across the terminals of each of the respective segments.

A clock 35 provides timing for the control system 11 such that, for one time period (0.2 ms) the constant current source 30 provides a low (1 ma) test current input to the heating element 13. During this interval (test period) resistance measurements are taken for each segment 13a–13n, from which the temperature of each segment is derived. During the remainder of the cycle (heating period) of the clock 35 (2 ms), a constant voltage is selectively applied to each segment 13a–13n through switch elements 36a–36n in accordance with the requirement of the particular segment.

The segment 13a for example represents one portion of the blade heating element 13 which may be operating at a selected temperature in accordance with whether or not it is in contact with incised tissue. If the segment 13a is in contact with tissue it will cool and its resistance will increase. If the voltage drop across the terminals 20a and 20b of the segment 13a during the test period increases above a value established by a set point 32a for segment 13a, then during the heating period a selected voltage will be applied across segment 13a by the control system 11. Thus for a constant current more power will be dissipated in the segment.

During the test portion of the cycle the voltage drop across the leads 20a and 20b for segment 13a is measured by a dedicated differential amplifier 31a via respective connections 20a' and 20b'. The differential amplifier 31a detects the potential across segment 13a and provides an amplified output of the absolute difference in the voltage across the segment 13a. The difference output is coupled to a comparator 33a. A previously mentioned set point circuit 32a for the segment 13a is set to a selected threshold which is a control input for the comparator 33a. The comparator 33a compares the voltage derived by the differential amplifier 31a with the set point 32a output. If this derived voltage is greater than that of the set point 32a, the comparator 33a will produce a corresponding ONE input for a logic 34a. If the voltage is less than the set point, a ZERO is transmitted to logic 34a. ZEROS and ONES are interpreted by logic 34a which provides a digital signal driving switches 36a which in turn gate power to the segment 13a. The logic 34a usually receives an additional reference input from an adjacent segment. In the case of segment 13a (the first in a series) a reference input 21 is fixed at the voltage of lead 20a' (ground).

Logic 34a has constraints which require that if more than one input is a ONE, the output is a ZERO, or if more than one input is a ZERO, its output is a ZERO. Thus in FIG. 2 if the input to logic 34a from comparator 33a is a ONE and the reference input from terminal 21 is also a ONE, its output is ZERO. Similarly if both inputs are ZERO's, its output is ZERO; but if either input is a ONE and the other is a ZERO the output will be a ONE. Although terminal 21 may be a ONE or ZERO as desired in the present example it is shown coupled to ground G and is a ZERO. This type of logic is known as an exclusive OR hereinafter described. By referencing the input of logic 34a to a previous segment (or ground reference 20a') the segment in question may be energized with an applied voltage which floats independent of the next previous segment.

The logic 34a determines the polarity of the output that should be provided, while switches 36a, gate power in accordance therewith. In a preferred embodiment the polarity of power gated by switches 36a may be either a positive voltage Vp or ground Vo. Thus the lead 20b may be provided with either a positive voltage Vp or may be set at ground Vo (shunted out). Similarly segment 13b is controlled both by a reference input 34a' from the prior logic 34a and the output of comparator 33b, which in turn is established by the voltage across the terminals 20b and 20c as derived by differential amplifier 31b via respective leads 20b' and 20c', and the set point 32b. The logic 34b detects the polarity of the previous segment 13a over lead 34a' of logic 34a.

Each segment 13a–13n of the heating element 13 has its own separate control circuit and is independent in its operations from each other segment. However each segment is dependent upon the previous segment (or a reference signal for the case of segment 13a) for its control polarity.

In order to more fully describe the apparatus of the present invention and its control, reference is directed to FIG. 3 wherein one segment 13c is described with its control logic, other portions of the control circuit 11 being eliminated for clarity. The equivalent circuit for the heating element 13 is the same as that described in FIG. 2, that is segments 13a through 13n are represented as a group of series connected resistors which may have values of resistance which vary depending upon the temperature. Connections 20c-20c' and 20d-20d' provide inputs for differential amplifier 31c which is enclosed in the dotted block so labeled. The inputs 20c'-20d' of the differential amplifier 31c are coupled through the input resistors 40 and provide normalized inputs over respective leads 45a-45b for an operational amplifier 41 contained therein. Zener diodes 42 establish a reference for the inputs and overload protection for the operational amplifier 41. Feedback resistors 43 preferably provide a differential gain of one in combination with input resistors 40.

The operational amplifier 41, provides an output at lead 44 which is either positive or negative depending upon the relative polarity of the inputs. If the voltage for segment 13c is established at a normalized +1V (ONE) for input 45a of operational amplifier 41, a positive output (ONE) will be produced on lead 44. On the other hand if a negative voltage of −1V is seen at the input 45b of the amplifier 41, a negative voltage (ZERO) will be produced. At any rate, the output of the differential amplifier 31c, is coupled via lead 44 to the input of the comparator 33c. This comparator 33c is known in the art simply as an operational amplifier 39c which has two inputs 44 and 49, the former input from the differential amplifier 31c, and the latter from the set point circuit 32c. The set point circuit 32c is essentially a potentiometer having a fixed input voltage source 46, a series connected load resistor 47 variable resistor 48 and wiper 48' for control. Set point 32c is coupled to input lead 49 of the operational amplifier 39c of comparator 33c. If the input 44 to the comparator 33c from differential amplifier 31c is less than the set point 32c a negative output (ZERO) will be produced. If the reverse is true a positive output (ONE) will be produced.

The ONE or ZERO output of comparator 33c is coupled to an exclusive OR gate 50c in logic 34c via lead 51. Exclusive OR gate 50c has one input 51 from the comparator 33c and a second input 34b' from the output of a previous exclusive OR gate 50b (not shown), in logic 34b illustrated in FIG. 2 for the segment 13b. As previously mentioned, the reason for providing prior signal from the segment 34b is to establish a reference polarity for the segment 13c with respect to an already established reference for the adjacent segment 13b. Thus the prior signal from the segment 13b permits the logic of the segment 13c to isolate itself from effects of adjacent circuitry. The exclusive OR gate 50c produces a positive output (ONE) if and only if one or the other of the inputs 51 or 34b' are positive. If both are negative or both positive, a negative output (ZERO) will be produced.

Logic 34c includes other circuitry for selectively energizing the switches 36c hereinafter described.

A flip flop 52 included in logic 34c receives the output from the exclusive OR gate 50c over lead 53. If the output of the exclusive OR gate 50c is positive (ONE), the Q output will go positive (ONE) and the $\overline{Q}$ will go negative (ZERO). AND gates 55a and 55b receive inputs from the respective Q and $\overline{Q}$ outputs of the flip flop 52. In addition the AND gates 55a and 55b receive an input over common lead 54 from the clock 35. During the heating portion of the clock cycle AND gates 55a and 55b and flip flop 52 receive a positive enable pulse (ONE) over respective leads 54 and 54' from clock 35. If the corresponding output Q or $\overline{Q}$ from the flip flop 52 is also a ONE the corresponding AND gate 55a or 55b will produce a positive output (ONE), which will allow a respective series connected light emitting diode 56a or 56b to conduct from a voltage source through its corresponding load 57a, 57b. The clock 35 resets flip flop 52 during the corresponding test portion of the cycle.

When either of the light emitting diodes 56a or 56b produce an output (light) it activates a corresponding portion of the switch circuit 36c.

It should be understood that only one of the light emitting diodes 56a or 56b may conduct at any one time. Thus the exclusive OR gate 50c, the flip flop 52 and the clock 35 operate and AND gates 55a and 55b in a manner such that only one is producing a ONE output at any one time.

Each of the light emitting diodes 56a and 56b are coupled via the respective light coupling (arrows 63a-63b) to a corresponding light responsive transistor 60a or 60b. When the diode 56a conducts and emits light the light responsive transistor 60a conducts and produces an input for a pair of Darlington connected transistors 61a through base connection 62a. Similarly when light emitting diode 56b conducts, it energizes the light responsive transistor 60b which drives the pair of Darlington connected transistors 61b on through base load resistor 62b.

In the present invention, when light emitting diode 56a conducts there will be produced a power output of Vp volts on the lead 37c which is coupled to input 20d of the segment 13c. On the other hand if the light emitting diode 56b conducts there will be produced a Vo volt signal along said lead 37c.

In a typical scanning cycle, a small current such as provided by the constant current source 30 (FIG. 2) is conducted through heating element 13, and a resultant voltage drop for each segment 13a-13n is measured by the corresponding differential amplifier 31a-31n. The voltage drop across each of the segments 13a through 13n is proportional to the resistance of each segment and thus by inference the temperature of each is determined. The resistance of each of the segments 13a-13n may be correlated to the set point 32a-32n value for establishing a threshold by which comparator 33a-33n through logic 34a-34n and switches 36a-36n energize the respective segment 13a-13n in accordance with necessary power requirements.

In FIG. 3, logic including exclusive OR gate 50c, flip flop 52c and AND gates 55a-55b assures that voltage from segment to segment is not cumulative but independent. In other words each of the segments has one common connection to its adjacent segment. Thus the exclusive OR circuit 34c and associated logic requires that, if segment 13c has a voltage supplying power thereto at one polarity, e.g. (+) and the next segment 13d also requires a power input, its power will be supplied at a corresponding opposite polarity (−), and the two adjacent segments 13c-13d will share a common terminal (20d). If the next segment 13d demands no power the polarity of the next segment will be the same as the previous one (+). Thus the net voltage across the particular segment requiring ZERO power is zero.

By sharing common terminals and by appropriate logic the present invention reduces the number of connections for the control of multiple segments of heating element 13 to n+1 connectors wherein n is the number of segments.

In the present invention a 3 ms duty cycle is contemplated. Clock 35 resets flip flops 52 (others not shown) for 0.2 ms for disabling AND gates 55a-55b etc. and switches 36c, etc. so that no power is applied to the corresponding segment 13c etc. During the next 2 ms, clock 35 allows exclusive OR gates 50c etc. to enable one or the other of the outputs of switches 36c etc. for powering or grounding the corresponding segment. The ON/OFF time is so short that, thermally, each segment maintains an average temperature over the duty cycle, which is sufficiently accurate for the measurements contemplated herein.

It is possible to control the relative intensity of the voltage applied on each segment 13a–13n by providing a variable potential or bias at Vp and Vo. Thus for a selected time interval the relative potential of applied power Vp or Vo can be adjusted so that the respective segment demands power for approximately 90% of the time interval selected. This may be accomplished by manual calibration techniques.

The present invention is useful for other applications requiring a heated cutting edge, notwithstanding the main thrust of the disclosure for a surgical instrument. For example, the invention could be used to cut thermoplastic material with simultaneous sealing of cut edges.

While there has been provided what at present is considered to be the preferred embodiment of the present invention it will be obvious to those skilled in the art that various changes and modifications may be made therein without departing from the invention, and it is intended in the appended claims to cover all such changes and modifications that fall within the true spirit and scope of the invention.

What is claimed is:

1. A surgical instrument for cutting tissue with simultaneous hemostasis, the instrument comprising: a substrate of electrically insulating material in the form of a blade having a cutting edge, having disposed thereon in the vicinity of the cutting edge an electrically heatable element of electrically conductive material exhibiting a resistance characteristic which varies as a function of the temperature, the heatable element being divided at selected locations into a plurality of independently heatable sections which form segments along said cutting edge and connection means for each segment providing electrical connection to each of said segments at the selected locations, means for independently supplying electrical power thereto along said connection means for maintaining the temperature of each of said segments at substantially constant selected value, said connection means including n+1 conductors for the heatable element wherein n is the number of segments, such that, the connection means for each pair of adjacent segments is shared by a common one of the n+1 conductors; logic means for coupling said means for supplying electrical power to each of said segments over said connection means independent of power supplied to an adjacent segment, such that, each may be heated independently, said logic means including exclusive OR logic for each segment, responsive to a reference polarity signal corresponding to the polarity of the power supplied at one of said connection means for the segment for producing selected outputs, means responsively coupled to the logic means for providing power to the segment in opposite electrical sense to the reference polarity signal for the segment or the same electrical sense to inhibit power thereto.

2. The surgical cutting instrument of claim 1 further including: test circuit means coupled to the heatable element for imposing a constant current along said heatable element, and sensing means parallel connected to each corresponding segment, for producing a voltage output corresponding to electrical resistance of the segment.

3. The surgical cutting instrument of claim 2 wherein the means for providing power to the corresponding segments includes circuit means for each segment responsive to the voltage output of the sensing means for maintaining the temperature of the corresponding segment substantially at a selected value.

4. The surgical cutting instrument of claim 3 wherein said sensing means includes: a differential amplifier operatively coupled to each corresponding segment for detecting the voltage output thereacross and for producing the voltage output as a function of resistance to thereby infer temperature for that segment; set point means for providing a preselected maximum output corresponding to a preselected maximum inferred temperature, and a comparator responsively coupled to the differential amplifier output and the set point means output for producing a ONE or ZERO output, said logic means responsive to said outputs for enabling power to be delivered to the corresponding segment if the set point means output and the differential amplifier output differ by a selected value.

5. The surgical cutting instrument as provided in claim 4 wherein said logic means including said exclusive OR logic for each segment is respectively responsively coupled to the comparator output for the corresponding segment and the reference polarity signal to produce respective control inhibit and enable outputs for said circuit means.

6. The surgical cutting instrument as provided in claim 5 wherein said circuit means further includes switch means responsively coupled to said logic means for gating power in appropriate polarities in accordance with the respective inhibit and enable control outputs thereof.

7. The surgical cutting instrument as provided in claim 6 wherein said exclusive OR logic produces respective ONE or ZERO outputs in response to the comparitor output and the reference polarity signal, the latter comprising a ONE or ZERO output of the exclusive OR logic for the previous segment.

8. The surgical cutting instrument as provided in claim 7 wherein said switch means is coupled to the connection means and gates each segment with at least one of two net potentials thereacross independent of the net potential applied to an adjacent segment but in accordance with the potential applied to one of the connection means for the adjacent segment, an extreme end one of the segments having its reference polarity signal supplied from said means for supplying power in one electrical sense only.

9. The surgical cutting instrument as provided in claim 1 wherein said electrically heatable element comprises a film deposited on the cutting edge of the blade, said film exhibiting a negative temperature coefficient of resistance.

10. A control system for a cutting instrument wherein a substrate of electrically insulating material in the form of a blade having a cutting edge has disposed thereon in the vicinity of the cutting edge an electrically heatable element of electrically conductive material exhibiting a resistance characteristic which varies as a function of the temperature, the element being divided at selected locations into a plurality of independently heatable sections which form segments along said cutting edge and connection means for each segment providing electrical connection to each of said segments at the selected locations, means coupled to the connection means for independently supplying electrical power to each segment for maintaining the temperature thereof at substantially constant selected value, said connection means including n+1 conductors for the heatable element wherein n is the number of segments, such that, the connection means for each pair of adjacent segments is shared by a common one of the n+1 conductors; the control system comprising: logic means for selectively governing power to each of said segments over said connection means independent of power supplied to an adjacent segment such that each may be heated independently, said logic means including exclusive OR logic for each segment, responsively coupled to a reference polarity signal established at one of said connection means for each segment for producing selected outputs, switch means responsively coupled to the selected outputs of the logic means and the means for supplying power for gating power to the segment in opposite electrical sense to the reference polarity signal established at said one of said connection means for the segment or in the same electrical sense to respectively enable or inhibit power thereto.

* * * * *

UNITED STATES PATENT AND TRADEMARK OFFICE
CERTIFICATE OF CORRECTION

PATENT NO. : 4,219,025
DATED : August 26, 1980
INVENTOR(S) : Donald M. Johnson

It is certified that error appears in the above-identified patent and that said Letters Patent are hereby corrected as shown below:

Column 1, line 23, "heated" should be changed to read --heating--.

Signed and Sealed this

Twenty-seventh Day of January 1981

[SEAL]

Attest:

RENE D. TEGTMEYER

Attesting Officer     Acting Commissioner of Patents and Trademarks